United States Patent [19]

Favre et al.

[11] Patent Number: 4,529,749

[45] Date of Patent: Jul. 16, 1985

[54] MICROORGANSIM-RESISTANT, SINGLE-COMPONENT RTV ORGANOPOLYSILOXANE COMPOSITIONS

[75] Inventors: Georges Favre, Feyzin; Patrice Perrin, Lyons, both of France

[73] Assignee: Rhone-Poulenc Specialites Chimiques, Courbevoie, France

[21] Appl. No.: 638,666

[22] Filed: Aug. 8, 1984

[30] Foreign Application Priority Data

Aug. 12, 1983 [FR] France ................... 83 13255

[51] Int. Cl.³ ............................... C08K 5/40
[52] U.S. Cl. ................... 523/122; 524/201; 524/588; 524/863
[58] Field of Search ............ 523/122; 524/201

[56] References Cited

U.S. PATENT DOCUMENTS 3,318,763  5/1967  Brooks et al. ............ 523/122
4,314,850  2/1982  Watanabe et al. ............ 524/178

FOREIGN PATENT DOCUMENTS 54-56651  5/1979  Japan ................... 524/201
57-96044  6/1982  Japan ................... 523/122

Primary Examiner—Lewis T. Jacobs
Attorney, Agent, or Firm—Burns, Doane, Swecker & Mathis

[57] ABSTRACT

Microorganism-resistant, storage-stable, single-component room temperature vulcanizable organopolysiloxane compositions, especially adapted as sealants, are comprised of:

(A) 100 parts of an $\alpha,\chi$-dihydroxydiorganopolysiloxane polymer;
(B) 2 to 25 parts of an organosilane;
(C) 5 to 200 parts of inorganic filler material;
(D) 0.0003 to 15 parts of a hardening catalyst; and
(E) 0.01 to 1.2% by weight, based upon the total weight of the composition, of at least one fungicidal tetraalkylthiuram disulfide.

6 Claims, No Drawings

MICROORGANSIM-RESISTANT, SINGLE-COMPONENT RTV ORGANOPOLYSILOXANE COMPOSITIONS

BACKGROUND OF THE INVENTION

1. Field of the Invention

The present invention relates to single-component organopolysiloxane compositions which are storage stable in the absence of moisture, harden or cure to elastomers beginning at room temperature in the presence of moisture and are microorganism resistant by virtue of incorporation therein of a particularly active fungicidal agent.

2. Description of the Prior Art

Single-component organopolysiloxane compositions have been in use for over 20 years as sealing materials in all fields of application which require resilient seals which efficiently withstand aging, inclement weather, heat and cold and the action of corrosive materials. In particular, in the field of sanitation they provide the sealing of the chinks present in bathrooms and kitchens, around baths, showers, sinks, tiling and the like. However, these seals very quickly lose their new attractive appearance as a result of the proliferation, on their surfaces, of molds which form dark-colored, unattractive areas and streaks.

Fungicidal agents have been introduced into organopolysiloxane compositions to resist the development of such microorganisms. However, not all of the known fungicidal agents commonly employed in agriculture or in the field of paints and coatings are suitable; in fact, their presence can have an undesirable effect, for example, on the stability of the compositions or on the adhesion of the elastomers produced by these compositions to various substrates (compare published European Application No. 34,877).

It is thus necessary to compromise when attempting to reconcile high antifungal effectiveness and the retention of good physical properties. This is precisely why numerous documents have been published and continue to be published on the subject of addition of antifungal compounds to organopolysiloxane compositions and elastomers.

Among the antifungal compounds described in the literature, exemplary are:

(1) 2-(4-Thiazolyl)benzimidazole (published French Application No. 2,421,195);
(2) Iodoalkylphenylsulfones (aforementioned European Application No. 34,877)
(3) Phenylmercury salts of carboxylic acids (French Pat. No. 1,462,754);
(4) 2,3,5,6-Tetrachloro-4-methylsulfonylpyridine (published Japanese Application No. 76/106,158);
(5) Oxides and other derivatives of triorganotin compounds (published Japanese Application Nos. 82/096,044 and 82/133,150).

SUMMARY OF THE INVENTION

It has now unexpectedly and surprisingly been found that, from among the known fungicidal agents, the tetraalkylthiuram disulfides, when dispersed in single-component organopolysiloxane compositions, demonstrate singularly high antifungal activity; furthermore, they do not alter or adversely affect the physical properties of such compositions or of the elastomers produced therefrom.

Briefly, the present invention features organopolysiloxane compositions containing at least one tetraalkylthiuram disulfide. More especially, a major object of this invention is the provision of improved single-component organopolysiloxane compositions, stable upon storage in the absence of water, hardening or curing to an elastomer beginning at ambient temperature in the presence of water, and formed by intimate admixture of the following components:

(A) 100 parts by weight of an $\alpha,\omega$-dihydroxydiorganopolysiloxane polymer, having a viscosity of 700 to 1,000,000 mPa.s at 25° C., comprising recurring siloxy units of the formula $R_2SiO$ in which the symbols R, which may be identical or different, denote hydrocarbon radicals containing from 1 to 8 carbon atoms, substituted or unsubstituted by halogen atoms or cyano groups;

(B) 2 to 25 parts by weight of an organosilane of the formula $R_aSi(Z)_{4-a}$ in which the symbol R has the meaning given under (A), and the symbols Z, which may be identical or different, denote hydrolyzable radicals selected from among those of the formulae:

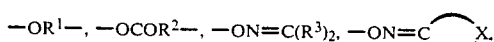

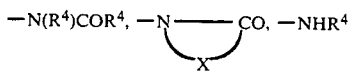

in which:

(i) the symbol $R^1$ denotes an alkyl radical containing from 1 to 4 carbon atoms, or a $\beta$-methoxyethyl radical of the formula $-CH_2CH_2OCH_3$,
(ii) the symbol $R^2$ denotes a hydrocarbon radical, devoid of aliphatic unsaturation, containing from 1 to 15 carbon atoms,
(iii) the symbols $R^3$, which may be identical or different, denote alkyl radicals containing from 1 to 5 carbon atoms,
(iv) the symbols $R^4$, which may be identical or different, denote hydrocarbon radicals devoid of aliphatic unsaturation, containing from 1 to 10 carbon atoms,
(v) the symbol X denotes an alkylene radical containing from 3 to 7 carbon atoms, and
(vi) the symbol a denotes zero or one;

(C) 5 to 200 parts by weight of inorganic fillers; and
(D) 0.0003 to 15 parts by weight of a hardening or curing catalyst selected from among iron and titanium chelates, the tin, iron or lead salts of carboxylic acids, organotin salts of carboxylic acids, alkyl titanates and zirconates, or the products of reaction of organotin salts of carboxylic acids with alkyl titanates, which composition comprises from 0.01 to 1.2% by weight, based on the total weight of the composition, of a fungicidal agent (E) comprising at least one tetraalkylthiuram disulfide having the formla (I):

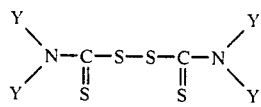

in which the radicals Y, which may be identical or different, denote an alkyl radical containing from 1 to 4 carbon atoms.

DETAILED DESCRIPTION OF THE INVENTION

More particularly, according to the present invention, the α,ω-dihydroxydiorganopolysiloxane polymers (A) having a viscosity of 700 to 1,000,000 mPa.s at 25° C., preferably 1,000 to 700,000 mPa.s at 25° C., are preferably linear polymers, essentially consisting of diorganosiloxy recurring units of the aforesaid formula $R_2SiO$, and blocked or chain terminated at each end of their polymer chain by a hydroxyl group; however, the presence of monoorganosiloxy units of the formula $RSiO_{1.5}$ and/or of siloxy units of the formula $SiO_2$ is not excluded in the proportion of at most 2% based on the number of diorganosiloxy recurring units.

The hydrocarbon radicals containing from 1 to 8 carbon atoms, substituted or unsubstituted with halogen atoms or cyano groups, denoted by the symbols R, include:

(a) alkyl and haloalkyl radicals containing from 1 to 8 carbon atoms, such as methyl, ethyl, n-propyl, isopropyl, n-butyl, n-pentyl, n-hexyl, 2-ethylhexyl, n-octyl, 3,3,3-trifluoropropyl, 4,4,4-trifluorobutyl, and 4,4,4-3,3-pentafluorobutyl radicals;

(b) cycloalkyl and halocycloalkyl radicals containing from 4 to 8 carbon atoms, such as cyclopentyl, cyclohexyl, methylcyclohexyl, 2,3-difluorocyclobutyl, and 3,4-diflouro-5-methylcycloheptyl radicals;

(c) alkenyl radicals containing from 2 to 4 carbon atoms such as vinyl, allyl and 2-butenyl radicals, (d) aryl and haloaryl radicals containing from 6 to 8 carbon atoms such as phenyl, tolyl, xylyl, chlorophenyl, dichlorophenyl and trichlorophenyl radicals, and (e) cyanoalkyl radicals, the alkyl moieties of which contain from 2 to 3 carbon atoms, such as β-cyanoethyl and γ-cyanopropyl radicals.

Exemplary of recurring units denoted by the formula $R_2SiO$, the following are representative:

```
(CH3)2SiO  CH3(CH2=CH)SiO  CH3(C6H5)SiO
(C6H5)2SiO  CF3CH2CH2(CH3)SiO
NC—CH2CH2(CH3)SiO
NC—CH(CH3)CH2(CH2=CH)SiO
NC—CH2CH2CH2(C6H5)SiO
```

It will be appreciated, according to one embodiment of the invention, that it is envisaged to employ as the polymers (A) a mixture comprising α,ω-dihydroxydiorganopolysiloxane polymers differing from each other in molecular weight and/or the nature of the substituent groups bonded to the silicon atoms.

These α,ω-dihydroxydiorganopolysiloxane polymers (A) are commercially available; moreover, they can readily be manufactured. One of the most widely used manufacturing techniques comprises, in a first stage, polymerizing diorganocyclopolysiloxanes with the aid of catalytic amounts of alkaline or acidic agents and then treating the polymerizates with calculated quantities of water (French Pat. Nos. 1,134,005, 1,198,749, and 1,226,745); this addition of water, which is proportionally increased as the viscosity of the polymers to be prepared is decreased, may be wholly or partly released by α,ω-dihydroxydiorganopolysiloxane oils of low viscosity, for example, ranging from 5 to 200 mPa.s at 25° C., containing a high proportion of hydroxyl radicals, for example, from 3 to 14%.

The crosslinking agents (B) are used in a proportion of 2 to 25 parts by weight, preferably 3 to 20 parts by weight, per 100 parts by weight of α,ω-dihydroxydiorganopolysiloxane polymers (A).

Same correspond to the aforementioned formula $R_a$-$Si(Z)_{4-a}$ in which the symbol R is defined as were the symbols R in the aforementioned $R_4SiO$ units, the symbol Z denotes, as above indicated, hydrolyzable radicals selected from among those of the formulae:

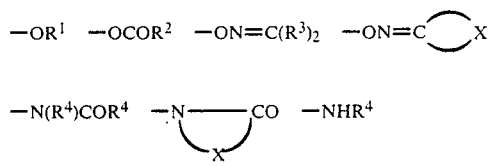

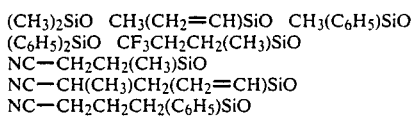

and the symbol a denotes zero or one.

The nature of the radicals denoted by the symbol R has been above described; details are now given regarding the nature of the radicals denoted by the other symbols. Thus, the symbol $R^1$ denotes a β-methoxyethyl radical, or an alkyl radical containing from 1 to 4 carbon atoms, such as the methyl, ethyl, n-propyl, isopropyl, n-butyl or tert.-butyl radicals.

The symbol $R^2$ denotes a hydrocarbon radical devoid of aliphatic unsaturation which includes:

(1) alkyl radicals containing from 1 to 15 carbon atoms, such as methyl, ethyl, n-propyl, n-butyl, n-pentyl, 1-ethylpentyl, n-hexyl, n-octyl, neodecyl, n-decyl, n-dodecyl and n-pentadecyl radicals;

(2) cycloalkyl radicals containing from 5 to 6 ring carbon atoms, such as cyclopentyl and cyclohexyl radicals; and (3) aryl radicals containing from 6 to 8 carbon atoms, such as phenyl, tolyl or xylyl radicals.

Each symbol $R^3$ denotes an alkyl radical containing from 1 to 5 carbon atoms, such as the methyl, ethyl, n-propyl, isopropyl, n-butyl, isobutyl or n-pentyl radicals.

Each symbol $R^4$ denotes a hydrocarbon radical, devoid of aliphatic unsaturation, which includes:

(1) alkyl radicals containing from 1 to 10 carbon atoms, such as methyl, ethyl, n-propyl, n-butyl, n-hexyl, 1-ethylpentyl, n-octyl or n-decyl radicals;

(2) cycloalkyl radicals containing from 5 to 8 carbon atoms, such as cyclopentyl, cyclohexyl, methylcyclohexyl or dimethylcyclohexyl radicals;

(3) aryl radicals containing from 6 to 8 carbon atoms, such as phenyl, tolyl or xylyl radicals.

The symbol X denotes a linear or branched chain alkylene radical containing from 3 to 7 carbon atoms which may be selected from those of the formulae:

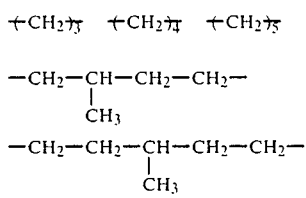

-continued
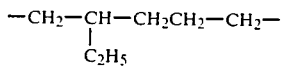

As aforesaid, the symbols Z of the formula $R_aSi(Z)_{4-a}$ may be identical or different. When they are identical, there must be, bonded to the silicon atom, 3 or 4 radicals of the same type, for example, radicals of the formula $-OR^1$ or the formula $-OCOR^2$. When they are different, there must be, bonded to the silicon atom, at least 2 radicals of a different type, for example, radicals of the formulae $-OCOR^2$ and $-NHR^4$ or the formulae $-ON=C(R^3)_2$ and $-N(R^4)COR^4$.

Among the silanes of the last-mentioned type, designated as mixed silanes, more particular consideration should be given, since they are well-known and easily prepared, to the silanes of the formula $R_aSi(Z')_b(OR^1)_{4-a-b}$ in which the symbols R, $R^1$ and a are as above defined, the symbol Z' has the same definition as Z except that it does not denote the radical $OR^1$, the symbol b denotes 1, 2 or 3 and the total of a+b is 1, 2 or 3. Furthermore, when 2 or 3 radicals denoted by Z' are bonded to the silicon atom (in which case b denotes 2 or 3), such radicals are almost always of the same type.

These mixed silanes are more particularly described in the first Certificate of Addition No. 90,695 to French Pat. No. 1,423,477 and in French Pat. Nos. 1,439,025, 1,541,542, 1,541,543 and 2,067,636.

The "standard" silanes, of the formula $R_aSi-(Z)_{4-a}$, in which all of the radicals denoted by Z are of the same type, are reflected in numerous patents, and more particularly in the following French Patents:

| | | |
|---|---|---|
| (1) | (Z = $OR^1$ radical) | (Nos. 1,330,625, 2,121,289, 2,121,631, and 2,458,572) |
| (2) | (Z = $-OCOR^2$ radical) | (Nos. 1,198,749, 1,220,348 and 2,464,288) |
| (3) | (Z = $-ON=C(R^3)_2$ or ON = C⌒X) | (Nos. 1,314,649, 1,371,250 and 2,074,144) |
| (4) | (Z = $-N(R^4)COR^4$ or N—CO⌒X) | (Nos. 1,423,477 and 2,201,326) |
| (5) | (Z = $-NHR^4$ radical) | (Nos. 1,248,826, 1,510,778 and 2,201,327) |

Referring to said patents, U.S. Pat. No. 2,458,572 describes alkoxyorganosilanes having the formula:

$$R^5{}_xSi[(OCH_2CH_2)_pOCH_3]_{4-x}$$

in which the symbol $R^5$ denotes a methyl, vinyl, allyl, methallyl, or phenyl radical, and the symbols p and x denote zero or 1.

After mixing with aminoorganosilanes, organotin salts and α,ω-dihydroxydiorganopolysiloxanes, these alkoxyorganosilanes produce compositions which are storage stable and which harden or cure to elastomers which strongly adhere to a wide variety of materials.

Representative silanes having the general formula $R_aSi(Z)_{4-a}$ are as follows:

(I) Normal silanes:

Z = $OR^1$
$Si(OCH_3)_4$, $CH_3Si(OCH_3)_3$, $CH_3Si(OCH_2CH_2OCH_3)_3$
$Si(OCH_2CH_2OCH_3)_4$, $CH_2=CHSi(OCH_2CH_2OCH_3)_3$
$C_6H_5Si(OCH_3)_3$, $C_6H_5Si(OCH_2CH_2OCH_3)_3$

Z = $OCOR^2$
$CH_3Si(OCOCH_3)_3$, $C_2H_5Si(OCOCH_3)_3$,
$CH_2=CHSi(OCOCH_3)_3$ $C_6H_5Si(OCOCH_3)_3$,
$CH_3Si\{OCOCH(C_2H_5)(CH_2)_3-CH_3\}_3$
$CF_3CH_2CH_2Si(OCOC_6H_5)_3$, $CH_3Si(OCOC_6H_5)_3$
$CH_3Si(OCOCH_3)_2OCOCH(C_2H_5)(CH_2)_3CH_3$
$CH_3COOSi\{OCOCH(C_2H_5)_2(CH_2)_3CH_3\}_3$

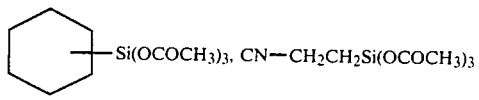

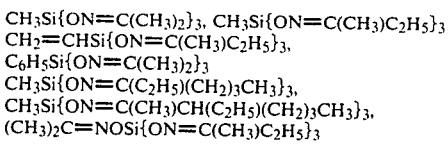

$CH_3Si\{ON=C(CH_3)_2\}_3$, $CH_3Si\{ON=C(CH_3)C_2H_5\}_3$
$CH_2=CHSi\{ON=C(CH_3)C_2H_5\}_3$,
$C_6H_5Si\{ON=C(CH_3)_2\}_3$
$CH_3Si\{ON=C(C_2H_5)(CH_2)_3CH_3\}_3$,
$CH_3Si\{ON=C(CH_3)CH(C_2H_5)(CH_2)_3CH_3\}_3$,
$(CH_3)_2C=NOSi\{ON=C(CH_3)C_2H_5\}_3$

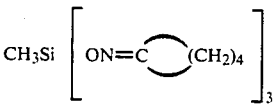

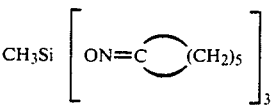

Z = $-N(R^4)COR^4$, 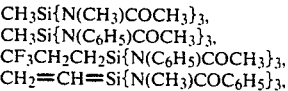

$CH_3Si\{N(CH_3)COCH_3\}_3$,
$CH_3Si\{N(C_6H_5)COCH_3\}_3$,
$CF_3CH_2CH_2Si\{N(C_6H_5)COCH_3\}_3$,
$CH_2=CH-Si\{N(CH_3)COC_6H_5\}_3$,

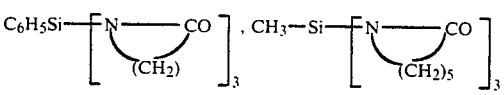

Z = $-NHR^4$

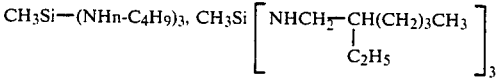

$C_6H_5Si(NH$ iso-$C_4H_9)_3$

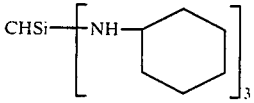

$CH_2=CHSi(NH-$iso-$C_4H_9)_3$ (II) Mixed silanes:
$CH_3Si(OCH_3)(OCOCH_3)_2$,

-continued
CH₂=CHSi(OCH₂CH₂OCH₃)(OCOCH₃)₂
(CH₃)₃CO—O—Si(OCOCH₃)₃
CH₃Si(OC₂H₅){ON=C(CH₃)₂}₂
CH₃Si(OCH₂CH₂OCH₃){ON=C(CH₃)₂}₂
CH₃Si(OCH₂CH₂OCH₃)₂[ON=C(CH₃)C₂H₅]
CH₃Si(OCH₃)[N(CH₃)COC₂H₅]₂
CH₃Si(OC₂H₅)₂[N(CH₃)COC₆H₅]

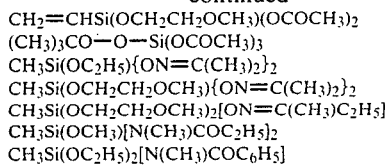

CH₃Si(OCOCH₃[NHCH(CH₃)₂]₂

(CH₃)₃C—OSi(OCOCH₃)[NHCH(CH₃)₂]₂
(C₂H₅O)₂Si(OCOCH₃)[NHCH(CH₃)₂]
CH₃Si(OC₂H₅)[N(CH₃)COC₆H₅]₂

The inorganic fillers (C) are incorporated in a proportion of 5 to 200 parts by weight, preferably 10 to 150 parts by weight, per 100 parts by weight of the α,ω-dihydroxydiorganopolysiloxane polymers (A).

These fillers may be incorporated in the form of very finely divided products, the mean particle diameter of which is less than 0.1 μm. Such fillers include pyrogenic silicas and precipitated silicas; their specific surface is typically greater than 40 m²/g.

These fillers may also be in the form of more coarsely divided materials, having a mean particle diameter greater than 0.1 μm. Exemplary of such fillers, representative are ground quartz, diatomaceous silicas, calcium carbonate, calcined clay, titanium oxide of rutile type, oxides of iron, zinc, chromium, zirconium or magnesium, the various forms of alumina (hydrated or not), boron nitride, lithopone, barium metaborate, barium sulfate and glass ballotini; their specific surface is typically less than 30 m²/g.

Fillers (C) may optionally have been surface-modified by treatment with the various organosilicon compounds conventionally employed for this purpose. Thus, these organosilicon compounds may be organochlorosilanes, diorganocyclopolysiloxanes, hexaorganodisiloxanes, hexaorganodisilazanes or diorganocyclopolysiloxanes (French Pat. Nos. 1,126,884, 1,136,885, 1,236,505; British Pat. No. 1,024,234). The treated fillers in the majority of cases contain from 3 to 30% of their weight of organosilicon compounds.

The fillers (C) may be composed of a mixture of several types of fillers of different particle size; thus, for example, they may be composed of 30 to 70% of finely divided silicas having a specific surface area greater than 40 m²/g and from 70 to 30% of more coarsely divided silicas having a specific surface less than 30 m²/g.

The hardening or curing catalyst (D) is employed in a proportion of 0.0003 to 15 parts by weight, preferably from 0.0005 to 12 parts by weight, per 100 parts by weight of the α,ω-dihydroxydiorganopolysiloxane polymers (A). It is selected from among:
(i) iron or titanium chelates, such as those of the formulae (the chelate bonds are not shown):

Fe[OC(CH₃)=CH—COCH₃]₃
(n-C₄H₉O)₂Ti[OC(CH₃)=CH—COCH₃]₂
(CH₃)₂CHO₃TiOC(CH₃)=CH—COOC₂H₅

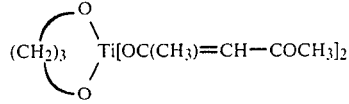

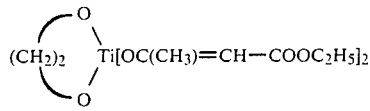

Other compounds are noted in French Pat. Nos. 1,330,625, 2,121,289 and 2,121,631;
(2i) tin, iron or lead salts of carboxylic acids, such as tin, iron or lead 2-ethylhexanoate, stearate, oleate or naphthenate;
(3i) organotin salts of carboxylic acids, such as di(n-butyl)tin diacetate and dilaurate, di(n-octyl)tin diacetate and dilaurate, dimethyltin di(2-ethylhexanoate), di(n-butyl)tin diversatate, di(n-octyl)tin succinate or di(n-octyl)tin maleate;
(4i) alkyl titanates and zirconates, such as those of the formulae:
(n-C₄H₉O)₄Ti, (C₂H₅O)₄Ti, [(CH₃)₂CHO]₄Ti (n-C₃H₇O)₄Ti, (n-C₈H₁₇O)₄Ti, (CH₃OCH₂CH₂O)₄Ti [CH₃(CH₂)₃CH(C₂H₅)CH₂O]₄Ti, (C₂H₅O)₄Zr, [(CH₃)₂CHO]₄Zr, (n-C₃H₇O)₄Zr (n-C₄H₉O)₄Zr, [(CH₃)₃C—O]₄Zr, (CH₃OCH₂CH₂O)₄Zr (n-C₇H₁₅O)₄Zr;
(5i) products of reaction of organotin salts of carboxylic acids (3i) with alkyl titanates (4i). These compounds contain Ti—O—Sn bonds; their preparation is described in French Pat. No. 1,392,648 and British Pat. No. 928,946.

The fungicidal agent (E) is introduced in a quantity such that it constitutes from 0.01 to 1.2% by weight, preferably from 0.03 to 1% by weight, based upon the total weight of the overall composition.

The compounds (E) which may be employed in accordance with the present invention are known compounds, the preparation of which is described particularly in U.S. Pat. Nos. 1,796,977 and 1,732,111 and by Cummings and Simmons, Ind. Eng. Chem., 20, 1173 (1928).

Exemplary of suitable compounds (E), representative are tetramethylthiuram disulfide, tetraethylthiuram disulfide and tetra-n-butylthiuram disulfide. The preferred fungicidal agent (E) according to the invention is tetramethylthiuram disulfide of the formula:

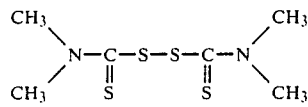

This is a white powder, the acute toxicity of which in mice is low: LD₅₀ on the order of 200 to 2,000 mg/kg.

Other than the components (A), (B), (C), (D), and (E), which are necessary for the preparation of the single-component compositions consistant herewith, there may be included an aminoorganosilane (F) in a proportion of 0.3 to 15 parts by weight, preferably 0.5 to 12 parts by weight, per 100 parts by weight of the α,ω-dihydroxydiorganopolysiloxanes (A). This aminosilane comprises at least one NH radical which is borne by an organic radical, which is bonded to the silicon atom via a C—Si bond.

More particularly, such aminoorganosilane (F) corresponds to the general formula:

$$YNH(G'X)_nGSi[(OCH_2CH_2)_pOR^6]_{3-m}Y'_m$$

in which:

(i) the symbol $R^6$ denotes a methyl or ethyl radical;
(ii) the symbol G denotes an alkylene radical containing from 1 to 5 carbon atoms;
(iii) the symbol X denotes an oxygen or sulfur atom;
(iv) the G' denotes an alkylene radical containing from 2 to 5 carbon atoms;
(v) the symbol Y denotes a radical of the formula $-(G''NH)_kR^7$ in which the symbol G'' denotes an alkylene radical containing from 2 to 6 carbon atoms; the symbol $R^7$ denotes a hydrogen atom or an alkyl radical containing from 1 to 4 carbon atoms, and the symbol k denotes zero, 1, 2 or 3;
(vi) the symbol Y' denotes a methyl, vinyl or phenyl radical;
(vii) the symbols p and n denote zero or 1; when p denotes 1 the symbol $R^6$ denotes only a methyl radical; and
(viii) the symbol m denotes zero, 1 or 2.

The alkylene radicals denoted by G, and G'' may be linear or branched chain; they correspond, for example (with the proviso that the number of carbon atoms defined above is taken into account for each symbol G, G' and G''), to the following formulae:

$$-CH_2-, \ -CH_2-CH_2-, \ -(CH_2)_3-$$
$$-CH_2-CH(CH_3)-, \ +CH_2+_4, \ -CH_2CH(CH_3)CH_2-$$
$$+CH_2+_5, \ +CH_2+_6, \ -CH_2-\underset{CH_3}{\underset{|}{CH}}-CH_2-CH_2-$$
$$-CH_2-CH_2CH(CH_3)CH_2CH_2-.$$

Furthermore, the alkyl radical denoted by the symbol $R^7$ may be a methyl, ethyl, n-propyl, isopropyl, n-butyl or isobutyl radical.

The aminoorganosilanes (F) may be divided into two groups, D1 and D2, depending on whether the symbol n respectively denotes zero or one; thus, the group D1 corresponds to the formula:

$$YNH-GSi[(OCH_2-CH_2)_pOR^6]_{3-m}Y'_m$$

and the group D2 to the formula:

$$YNHG'XGSi[(OCH_2CH_2)_pOR^6]_{3-m}Y'_m$$

Exemplary of aminoorganosilanes of the group D1, representative are those of the formulae:

$H_2N(CH_2)_3Si(OCH_2CH_2OCH_3)_3$,
$H_2N(CH_2)_3Si(OC_2H_5)_3$  $H_2N(CH_2)_3Si(OCH_3)_3$,
$HN(C_2H_5)CH_2Si(OCH_3)_3$
$H_2N(CH_2)_2NH(CH_2)_3Si(OCH_3)_3$,
$H_2N(CH_2)_2NH(CH_2)_3Si(OCH_2CH_2OCH_3)_3$,
$H(NHCH_2CH_2)_2NH(CH_2)_3SiCH_3(OCH_3)_2$.

Exemplary of aminoorganosilanes of the group D2, representative are those of the formulae:

$H_2N(CH_2)_3O(CH_2)_3Si(OCH_2CH_2OCH_3)_3$,
$HN(CH_3)(CH_2)_3O(CH_2)_3Si(OCH_3)_3$,
$H_2N(CH_2)_2S(CH_2)_3Si(OCH_3)_3$,
$H(NHCH_2CH_2)_2S(CH_2)_3SiCH_3(OCH_3)_2$.

These various aminoorganosilanes are per se known; they are described in particular in U.S. Pat. Nos. 2,754,311, 2,832,754, 2,930,809, 2,971,864, 3,341,563, 3,488,373, 3,551,375 and 3,598,853.

Their presence among the various components (A), (B), (C), (D) and (E), the mixture of which circumscribes the compositions according to the invention, has the effect of stabilizing the subject compositions and/or improving their adhesion to the materials with which they will be in contact.

A part, or all of the aminoorganosilanes (F) may be replaced by polymeric products produced by partial hydrolysis of these silanes. It is recommended that these hydrolysis products should still be soluble in the usual organic solvents at a concentration of at least 5 parts in 100 parts of solvent. The latter may include aliphatic, cycloaliphatic, aromatic, halogenated or non-halogenated hydrocarbons, such as n-octane, cyclohexane, methylcyclohexane, toluene, xylene, cumene, decalin, perchloroethylene, chlorobenzene and ortho-dichlorobenzene.

Similarly, a part or all of the aminoorganosilanes (F) may be replaced by aminoorganopolysiloxanes containing at least one NH group borne by an organic radical, which organic radical is bonded to a silicon atom via a C—Si bond; in particular, these aminoorganopolysiloxanes can be produced by a previous condensation of an aminoorganosilane (F) with a dihydroxydiorganopolysiloxane.

Polymers of this type are described in Belgian Pat. No. 774,830, U.S. Pat. No. 3,686,357, published European Application No. 50,453, and French Pat. Nos. 1,381,590, 1,385,693 and 2,228,814.

A preparative process which is more particularly advantageous is that described in the aforesaid French Pat. No. 2,228,814; same comprises reacting trialkoxylated aminoorganosilanes with hydroxylated methylpolysiloxanes in which at least 2% of the hydroxyl groups are bonded to the silicon atoms, as determined by titration. These methylpolysiloxanes have a viscosity ranging from 1 mPa·s at 25° C. to 1,000 mPa·s at 25° C. and correspond to the following general formula:

$$(CH_3)_{a'}(HO)_{b'}SiO_{\frac{4-a'-b'}{2}}$$

in which the symbol a' denotes any number from 1.6 to 2.3 and the symbol b' denotes any number from 0.1 to 1.

Apart from the components (A), (B), (C), (D), (E) and, if appropriate, (F) employed for the preparation of the compositions according to the invention, the usual adjuvants and additives may also be added, such as heat stabilizers. These compounds improve the heat resistance of the silicone elastomers produced by hardening the single-component compositions; same may be selected from among the salts of carboxylic acids, rare earth oxides and hydroxides, and more particularly ceric oxides and hydroxides, as well as from pyrogenic titanium dioxide and various iron oxides. From 0.1 to 15 parts by weight, preferably from 0.15 to 12 parts by weight, of heat stabilizers per 100 parts by weight of α,ω-dihydroxydiorganopolysiloxanes (A) are advantageously included.

In addition to these adjuvants, there may also be added organosilicon compounds which are capable of affecting the physical properties of the single-component compositions and/or the mechanical properties of the silicone elastomers derived therefrom upon hardening. These compounds are per se well known; they include, for example:

(1) α-ω-bis(triorganosiloxy)diorganopolysiloxane polymers having a viscosity of at least 10 mPa·s at 25° C. in which the organic radicals bonded to the silicon atoms are selected from methyl, vinyl or phenyl radicals; α,ω-bis(trimethylsiloxy)dimethylpolysiloxane oils having a viscosity of 10 mPa·s at 25° C. to 1,000 mPa·s at 25° C., are preferably incorporated;

(2) branched, liquid methylpolysiloxane polymers containing from 0.1 to 8% of hydroxyl groups bonded to the silicon atoms, comprising $(CH_3)_3SiO_{0.5}$, $(CH_3)_2SiO$, and $CH_3SiO_{1.5}$ units distributed such as to provide a $(CH_3)_3SiO_{0.5}/(CH_3)_2SiO$ ratio of 0.01 to 0.15 and a $CH_3SiO_{1.5}/(CH_3)_2SiO$ ratio of 0.1 to 1.5;

(3) α,ω-dihydroxydimethylpolysiloxane oils having a viscosity of 10 to 300 mPa·s at 25° C. and α,ω-dihydroxymethylphenylpolysiloxane oils having a viscosity of 200 to 600 mPa·s at 25° C.; and (4) diphenylsilanediol or 1,1,3,3-tetramethyldisiloxanediol.

The α,ω-bis(triorganosiloxy)diorganopolysiloxane polymers referred to above may be replaced wholly or in part by organic compounds which are unreactive towards the components (A), (B), (C), (D), (E) and (F) and which are miscible at least with the α,ω-dihydroxydiorganopolysiloxane polymers (A). Exemplary of such organic compounds, representative are the polyalkylbenzenes produced by alkylation of benzene with long-chain olefins, particularly the olefins containing 12 carbon atoms produced by propylene polymerization. Organic compounds of this type are reported, for example, in French Pat. Nos. 2,392,476 and 2,446,849.

To formulate the compositions according to the invention, it is advantageous to use apparatus which makes it possible to intimately admix, with the exclusion of moisture, with or without heat input, the components (A), (B), (C), (D), (E), to which may be added, if appropriate, the organosilanes (F) and the aforementioned adjuvants and additives.

All of these ingredients may be charged into the apparatus in any order of addition whatsoever. Thus, it is possible to first mix the α,ω-dihydroxydiorganopolysiloxane oils (A) and the fillers (C) and to then add to the resulting paste the organosilanes (B), the catalysts (D) and the fungicidal agent (E).

It is also possible to mix the oils (A) and the organosilanes (B) and to subsequently add to the homogenous reaction products of these two components (A) and (B), the fillers (C), the catalysts (D) and the fungicidal agent (E). During these operations, the mixtures may be heated to a temperature in the range 50°–180° C. under atmospheric pressure or under a reduced pressure in order to promote the removal of volatile substances such as water, polymers of low molecular weight, organic acids or oximes.

It is suggested, however, when a temperature of 100° C. is exceeded, to incorporate the fungicidal agent (E) last, into the cooled mixtures, the temperature of which is well below 100° C. This technique avoids possible decomposition of the fungicide due to impurities present in the various constituents and even in the fungicide. Furthermore, it is advantageous to introduce the fungicide (E) in the form of a paste produced by intimately admixing same with a triorganosiloxy-blocked and/or hydroxy-blocked diorganopolysiloxane oil, to facilitate its dispersion in the subject single-component compositions.

The compositions prepared in this manner may be employed as such, or in the form of dispersions in organic diluents. These diluents are, preferably, typical commercially available materials selected from among:

(1) aliphatic, cycloaliphatic, aromatic, halogenated or non-halogenated hydrocarbons, such as n-heptane, n-octane, cyclohexane, methylcyclohexane, toluene, xylene, mesitylene, cumene, tetralin, decalin, perchloroethylene, trichloroethane, tetrachloroethane, chlorobenzene, or orthodichlorobenzene;

(2) aliphatic and cycloaliphatic ketones, such as methyl ethyl ketone, methyl isobutyl ketone, cyclohexanone or isophorone; and (3) esters, such as ethyl acetate, butyl acetate or ethyloxyethanol acetate.

The amounts of diluents which are added must be adequate to produce stable dispersions which are easily spread on and over the substrate. These amounts depend substantially on the nature and the viscosity of the initial organopolysiloxane compositions. They may, therefore, vary widely in their proportions; nevertheless, it is recommended to formulate dispersions containing from 15 to 85% by weight of diluents.

The compositions according to the invention, employed as such, that is to say undiluted, or in the form of dispersions in diluents, are storage stable in the absence of water and harden even at room temperature (after removal of the solvents in the case of dispersions), in the presence of water, to form elastomers.

After the compositions employed as such are deposited onto solid substrates, in a moist atmosphere, it is found that a process of hardening or curing to elastomers commences; it takes place from the outside to the inside of the deposited material. A skin is first formed on the surface, then the crosslinking continues into the depths of the substrate. The complete formation of the skin, which is manifested by a non-sticky feel of the surface, requires a period of time which may range from 1 minute to 55 minutes; this time period depends upon the degree of relative humidity in the atmosphere surrounding the compositions and the ease with which they crosslink.

On the other hand, the hardening of the deposited layers into the depth of the substrate, which must be adequate to permit the demolding, or release, and handling of the formed elastomers, requires a longer period of time. In fact, this period depends not only upon the factors mentioned above in respect of the production of a non-sticky feel, but also on the thickness of the deposited layers, which generally ranges from 0.5 mm to several centimeters. This longer period of time may be from 10 minutes to 20 hours.

Once hardened to elastomers, the compositions (particularly those containing aminoorganosilanes (F)) can adhere to various substrates without the previous application of an anchoring agent.

The subject compositions may be employed for many applications, such as grouting in the building industry, assembly of the most diverse materials (metals, plastics, natural and synthetic rubbers, wood, cardboard, porcelain, brick, ceramics, glass, stone, concrete or building components), insulation of electrical conductors, encapsulation of electronic circuits, and preparation of molds serving for the manufacture of articles made of synthetic resins or foams.

The abovementioned dispersions of these compositions in diluents can be used for thin-layer impregnation of woven and non-woven products and articles, and coating sheets of metal or plastic or cellulose-based materials. The deposition can be carried out, for example, by dipping or by spraying; in the latter case, use is made of a paint spray-gun which makes it possible to produce homogeneous coatings 5 to 300 μm in thickness. After the dispersions are sprayed, the diluents evaporate and the compositions thus provided harden into a rubbery film.

These compositions, diluted or not, are more especially used in all the areas of application which are exposed to conditions promoting the development of microorganisms and molds. This is the case, for example, for the grouting of sanitary apparatus, encapsulation of electronic circuits employed in a hot and moist atmosphere; and coating of textiles or leathers which are also used in a hot and moist atmosphere.

In order to further illustrate the present invention and the advantages thereof, the following specific examples are given, it being understood that same are intended only as illustrative and in nowise limitative.

EXAMPLE 1

The following materials were intimately admixed in a first mixer:
(i) 100 parts by weight of an α,ω-dihydroxydimethylpolysiloxane oil having a viscosity of 20,000 mPa.s at 25° C.;
(ii) 56.5 parts by weight of titanium dioxide of rutile type, having a mean particle diameter of 5 microns; and
(iii) 6.55 parts or 19.5 parts by weight of a fungicidal agent which was either tetramethylthiuram disulfide of the formula:

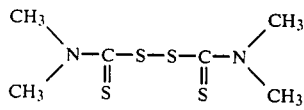

or tri(n-butyl)tin oxide of the formula $(n-C_4H_9)_3-Sn-O-Sn-(n-C_4H_9)_3$.

The mixing time was on the order of 3 hours. A white, homogeneous past (E) was obtained, containing either 4% or 11% of the antifungal agent.

A control (E1) was formulated using the same operational procedure by replacing the 6.55 parts by weight of antifungal agent with 6.55 parts by weight of titanium dioxide of rutile type.

The following materials were intimately admixed in a second mixer:
(i) 100 parts by weight of an α,ω-dihydroxydimethylpolysiloxane oil having a viscosity of 80,000 mPa.s at 25° C.,
(ii) 16 parts by weight of a methylpolysiloxane oil having a viscosity of 60 mPa.s at 25° C., containing 0.9% of hydroxyl groups bonded to the Si atoms, and comprising $(CH_3)_3SiO_{0.5}$, $(CH_3)_2SiO$ and $CH_3SiO_{1.5}$ units, distributed such as to provide a $(CH_3)_3SiO_{0.5}/(CH_3)_2SiO$ ratio of 0.04 and a $CH_3SiO_{1.5}/(CH_3)_2SiO$ ratio of 0.4; and
(iii) 14 parts by weight of a pyrogenic silica having a specific surface of 200 m²/g, treated with octamethylcyclotetrasiloxane.

The contents of this mixer were mixed for 2 hours at 150° C. under a gentle stream of dry nitrogen. After cooling the contents to approximately 40° C., 6.5 parts by weight of the above past (E), 6 parts by weight of methyltriacetoxysilane and 0.004 part by weight of n-butyl titanate were added thereto. The entire mass was mixed for 1 hour. A homogeneous self-curing composition containing either 0.18% or 0.5% by weight, based on the total weight of the composition, of one of the two antifungal agents was obtained.

The composition was spread with the aid of a spreader upon sheets of polyethylene arranged in the open air. The pasty layer which was deposited 2 mm in thickness, hardened and was converted into a rubbery plate. This plate was peeled off from the surface of the polyethylene sheets 24 hours after spreading the pasty layer; it was then permitted to stand for 7 days in the open air. Circular specimens 20 mm in diameter were then cut from this plate with the aid of a hollow punch.

These specimens, designated "normal", were exposed to the influence of various molds by following the tests for determining infestation resistance, according to the French Standard AFNOR X 41,514. The specimens were thus placed for 1 month at an incubation temperature of 30°±2° C. and at a relative humidity of 95%±5% in contact with the test molds employed, the latter including:
(1) *Aspergillus niger*
(2) *Aspergillus amstelodami*
(3) *Aspergillus flavus*
(4) *Penicillium brevi-compactum*
(5) *Penicillium cyclopium*
(6) *Paecilomyces varioti*
(7) *Trichoderma viride*
(8) *Chaetomium globosum*
(9) *Myrothecium verrucaria*
(10) *Stachybotrys atra*
(11) *Memnoniella echinata*
(12) *Penicillium funiculosum*

Specimens which had previously been subjected to various treatments (washing, exposure to ultraviolet radiation) were also placed in contact with the aforementioned molds.

The washing treatment consisted of placing the specimens for 48 hours in distilled water heated to 45° C.±2° C., in a proportion of 1 g of specimen per 100 g of water; the specimens were then left in contact with the molds for 4 months at 30° C.±2° C.

The treatment of exposure to the ultraviolet radiation consisted of exposing the specimens to radiations of wavelengths in the range 250–260 nm for 24 hours. The specimens were left in contact with the molds for 4 months at 30° C.±2° C.

The specimens were also exposed to soil microorganisms by following the tests using burial in soil according to the abovementioned French Standard NF X 41,514. According to the procedure developed in this standard, the specimens designated "normal" were buried in a strongly humus-bearing soil, with a pH of 6 to 7.5, moisture content of 30%±2%, heated to 30° C.±2° C.; they were permitted to remain in this state for 3 months.

The activity of the antifungal agents comprising the organopolysiloxane compositions was estimated by observing the degree of infestation of the specimens by the microorganisms. The following code was employed:
0 = nil growth, specimen intact
1 = growth over 25% of the specimen surface 2 = growth over 50% of the specimen surface
3 = growth over 75% of the specimen surface
4 = growth over 100% of the specimen surface.

The results of these various tests are reported in the Table I which follows:

TABLE I

| ANTIFUNGAL AGENT | | SENSITIVITY TO MOLDS | | | SENSITIVITY TO SOIL MICROORGANISMS |
|---|---|---|---|---|---|
| NATURE OF THE COMPOSITION | CONCENTRATION IN % | Specimen Normal, Untreated | Specimen Washed With Water | Specimen Exposed to Ultraviolet Radiation | |
| No antifungal agent, control batch | 0 | 4 | 4 | 4 | 4 |
| Tetramethyl- thiuram disulfide | 0.18 | 0 | 0 | 0 | 0 |
| | 0.5 | 0 | 0 | 0 | 0 |
| Tri (n-butyl)- tin | 0.18 | 0.5 | 1 | 1 | 0.5 |
| | 0.5 | 0 | 0.5 | 0.5 | 0 |

From the results reported in Table I, it was concluded that the tetramethylthiuram disulfide was markedly more active than tri(n-butyl)tin oxide.

EXAMPLE 2

The following materials were introduced into a mixer:
(i) 100 parts by weight of an α,ω-dihydroxydimethylpolysiloxane oil having a viscosity of 150,000 mPa.s at 25° C.;
(ii) 40 parts by weight of an α,ω-bis(trimethylsiloxy)-dimethylpolysiloxane oil having a viscosity of 20 mPa.s at 25° C.;
(iii) 4 part by weight of diphenylsilanediol;
(iv) 15 parts by weight of a pyrogenic silica having a specific surface of 200 m²/g; and
(v) 45 parts by weight of calcium carbonate having a mean particle diameter of 5 microns.

The contents of the mixer were intimately admixed for 2 hours at approximately 100° C. under a stream of dry nitrogen. After cooling to approximately 40° C., 11.3 parts by weight of the paste (E) employed in Example 1 and containing either 4% or 11% of the tetramethylthiuram disulfide were added to the mixture, successively followed by:
(a) 8 parts by weight of the silane of the formula Si(OCH$_2$CH$_2$OCH$_3$)$_4$;
(b) 3 parts by weight of the silane of the formula H$_2$NCH$_2$CH$_2$NH(CH$_2$)$_3$—Si(OCH$_3$)$_3$; and
(c) 0.07 parts by weight of dibutyltin dilaurate.

The mixture was intimately admixed for a few minutes. A homogeneous composition (C1) was obtained, which did not flow in a vertical position, and was storage stable in the absence of moisture.

Into a second mixer the following materials were introduced:
(i) 100 parts by weight of an α,ω-dihydroxydimethylpolysiloxane oil having a viscosity of 18,000 mPa.s at 25° C.;
(ii) 18 parts by weight of an α,ω-bis(trimethylsiloxy)-dimeethylpolysiloxane gum having a viscosity of 40,000 mPa.s at 25° C.;
(iii) 6 parts by weight of an α,ω-dihydroxymethylphenylpolysiloxane oil having a viscosity of 350 mPa.s at 25° C.;
(iv) 12 parts by weight of pyrogenic silica having a specific surface of 200 m²/g; and
(v) 12 parts by weight of lithopone having a mean particle diameter of 1 micron.

The contents of this mixer were intimately admixed for 4 hours at 150° C. under a stream of dry nitrogen.

After the mixture had cooled to approximately 50° C., the following materials were successively added:
(a) 8.2 parts by weight of the paste (E) employed in Example 1, containing either 4% or 11% of the tetramethylthiuram disulfide;
(b) 8.5 parts by weight of the crosslinking agent of the formula CH$_2$=CHSi[ON=C(C$_2$H$_5$)CH$_3$]$_3$; and
(c) 0.01 part by weight of n-butyl titanate.

The mixture was intimately admixed for 2 hours. A homogeneous composition (C2) was obtained, which was storage stable in moistureproof containers.

The following materials were introduced into a third mixer:
(i) 100 parts by weight of an α,ω-dihydroxydiorganopolysiloxane oil having a viscosity of 50,000 mPa.s at 25° C., containing 95% of (CH$_3$)$_2$SiO units and 5% of CH$_3$(CH$_2$=CH)SiO units;
(ii) 20 parts by weight of a liquid mixture having a viscosity of 90 mPa.s at 25° C., comprising organic compounds having boiling points of 302°–385° C. at atmospheric pressure, originating from a distillation fraction of branched dodecylbenzene;
(iii) 1 part by weight of an α,ω-dihydroxymethylphenylpolysiloxane oil having a viscosity of 350 mPa.s at 25° C.;
(iv) 15 parts by weight of pyrogenic silica having a specific surface of 200 m²/g, treated with octamethylcyclotetrasiloxane; and
(v) 130 parts by weight of calcium carbonate having a mean particle size of 5 microns.

The contents of the mixer were intimately admixed for 3 hours at a temperature of 120° C. under a gentle stream of dry nitrogen.

After the mixture had cooled to approximately 40° C., the following materials were successively added thereto:
(a) 15 parts by weight of the paste (E) employed in Example 1, containing either 4% or 11% of tetramethylthiuram disulfide;
(b) 18 parts by weight of the silane of the formula CH$_3$Si—[OCOCH(C$_2$H$_5$)(CH$_2$)$_3$CH$_3$]$_3$; and
(c) 0.008 part by weight of n-butyl titanate.

The entire mass was intimately admixed for 1 hour. A homogeneous single-component composition was obtained which was storage stable in the absence of moisture.

Each of the compositions (C1), (C2), and (C3) contained either 0.2% or 0.55% of tetramethylthiuram disulfide.

After hardening to elastomers in the open air, these compositions were placed in contact with molds and soil microorganisms, using the method described in Example 1.

The test results are reported in Table II below, from which it was concluded that essentially no development of molds and microorganisms occurred on the entire group of specimens.

TABLE II

| NATURE OF THE COMPOSITION | CONCENTRATION OF THE FUNGICIDAL AGENT, IN % | SENSITIVITY TO MOLDS | | | SENSITIVITY TO MICROORGANISMS |
|---|---|---|---|---|---|
| | | Specimen Normal, Untreated | Specimen Washed With Water | Specimen Exposed to Ultraviolet Radiation | |
| COMPOSITION C$_1$ | 0 control | 4 | 4 | 4 | 4 |
| | 0.2 | 0 | 0 | 0.5 | 0.5 |
| | 0.55 | 0 | 0 | 0 | 0 |
| COMPOSITION C$_2$ | 0 control | 4 | 4 | 4 | 4 |
| | 0.2 | 0 | 0 | 0.5 | 0 |
| | 0.57 | 0 | 0 | 0 | 0 |
| COMPOSITION C$_3$ | 0 control | 4 | 4 | 4 | 4 |
| | 0.2 | 0 | 0 | 0 | 0 |
| | 0.55 | 0 | 0 | 0 | 0 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A storage-stable, single-component RTV organopolysiloxane composition, comprising:

(A) 100 parts of an α,ω-dihydroxydiorganopolysiloxane polymer, having a viscosity of 700 to 1,000,000 mPa.s at 25° C., comprising diorganosiloxy recurring units of the formula R$_2$SiO in which the symbols R, which may be identical or different, are hydrocarbon radicals containing from 1 to 8 carbon atoms, or halo or cyano substituted such hydrocarbon radicals;

(B) 2 to 25 parts of an organosilane of the formula R$_a$Si(Z)$_{4-a}$ in which the symbol R is as above defined, and the symbols Z, which may be identical or different, are selected from among the hydrolyzable radicals of the formulae:

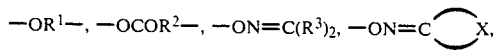

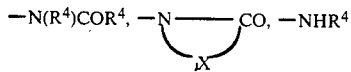

in which:

(i) the symbol R$^1$ is an alkyl radical containing from 1 to 4 carbon atoms, or a β-methoxyethyl radical of the formula —CH$_2$CH$_2$OCH$_3$;

(ii) the symbol R$^2$ is a hydrocarbon radical devoid of aliphatic unsaturation and containing from 1 to 15 carbon atoms;

(iii) the symbols R$^3$, which may be identical or different, are alkyl radicals containing from 1 to 5 carbon atoms;

(iv) the symbols R$^4$, which may be identical or different, are hydrocarbon radicals devoid of aliphatic unsaturation and containing from 1 to 10 carbon atoms;

(v) the symbol X is an alkylene radical containing from 3 to 7 carbon atoms; and (vi) the symbol a is zero or one;

(C) 5 to 200 parts of inorganic filler material;

(D) 0.0003 to 15 parts of a hardening catalyst comprising iron and titanium chelates, the tin, iron or lead salts of carboxylic acids, organotin salts of carboxylic acids, alkyl titanates and zirconates, or the products of reaction of organotin salts of carboxylic acids with alkyl titanates; and (E) 0.01 to 1.2% by weight, based upon the total weight of the composition, of at least one fungicidal tetraalkylthiuram disulfide having the formula (I):

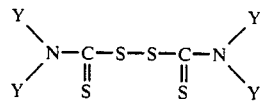

in which the radicals Y, which may be identical or different, are alkyl radicals containing from 1 to 4 carbon atoms.

2. The organopolysiloxane composition as defined by claim 1, comprising from 0.03 to 1% by weight of said fungicidal tetraalkylthiuram disulfide (E).

3. The organopolysiloxane composition as defined by claim 1, said fungicidal tetraalkylthiuram disulfide (E) comprising tetramethylthiuram disulfide, tetraethylthiuram disulfide or tetra-n-butylthiuram disulfide.

4. The organopolysiloxane composition as defined by claim 1, further comprising (F) from 0.3 to 15 parts, per 100 parts of the α,ω-dihydroxydiorganopolysiloxanes (A), of an aminoorganosilane which comprises at least one organic moiety bonded to a silicon atom via a C—Si bond.

5. The organopolysiloxane composition as defined by claim 4, said aminoorganosilane (F) having the general formula:

in which:

(i) the symbol R$^6$ is a methyl or ethyl radical;

(ii) the symbol G is an alkylene radical containing from 1 to 5 carbon atoms;

(iii) the symbol X is an oxygen atom or a sulfur atom;

(iv) the symbol G' is an alkylene radical containing from 2 to 5 carbon atoms;

(v) the symbol Y is a radical of the formula —(G"NH)$_k$R$^7$ in which the symbol G" is an alkylene radical containing from 2 to 6 carbon atoms; the symbol $R^7$ is a hydrogen atom or an alkyl radical containing from 1 to 4 carbon atoms, and the symbol k is zero, 1, 2 or 3;
(vi) the symbol Y' is a methyl, vinyl or phenyl radical;
(vii) the symbols p and n are zero or 1; with the proviso that when p is 1, the symbol $R^6$ can only be a methyl radical; and
(viii) the symbol m is zero, 1 or 2.

6. The organopolysiloxane composition as defined by claim 1, in hardened state.

* * * * *